(12) United States Patent
Li et al.

(10) Patent No.: US 11,345,709 B2
(45) Date of Patent: May 31, 2022

(54) PROCESS FOR PREPARING 4-(4-FLUORO-3-(2-(TRIFLUOROMETHYL)-5,6,7,8-TETRAHYDRO-[1,2,4]TRIAZOLO[1,5-A] PYRAZINE-7-CARBONYL)BENZYL) PHTHALAZIN-1(2H)-ONE

(71) Applicant: JIANGSU HENGRUI MEDICINE CO., LTD., Jiangsu (CN)

(72) Inventors: Wenhai Li, Lianyungang (CN); Yingjie Zhang, Lianyungang (CN)

(73) Assignee: JIANGSU HENGRUI MEDICINE CO., LTD., Jiangsu (CN)

( * ) Notice: Subject to any disclaimer, the term of this patent is extended or adjusted under 35 U.S.C. 154(b) by 0 days.

(21) Appl. No.: 16/960,117

(22) PCT Filed: Jan. 8, 2019

(86) PCT No.: PCT/CN2019/070797
§ 371 (c)(1),
(2) Date: Jul. 6, 2020

(87) PCT Pub. No.: WO2019/137358
PCT Pub. Date: Jul. 18, 2019

(65) Prior Publication Data
US 2021/0070760 A1 Mar. 11, 2021

(30) Foreign Application Priority Data

Jan. 9, 2018 (CN) .......................... 201810019736.1
Dec. 18, 2018 (CN) .......................... 201811547590.4

(51) Int. Cl.
C07D 487/04 (2006.01)
(52) U.S. Cl.
CPC .................................. C07D 487/04 (2013.01)
(58) Field of Classification Search
CPC .................................................... C07D 487/04
USPC ........................................................ 544/350
See application file for complete search history.

(56) References Cited

U.S. PATENT DOCUMENTS 9,273,052 B2  3/2016  Tang et al.
9,566,277 B2  2/2017  Tang et al.
(Continued)

FOREIGN PATENT DOCUMENTS

CN  102686591 A   9/2012
JP  2008063256 A   3/2008
(Continued)

OTHER PUBLICATIONS

D'Amours et al., "Poly(ADP-ribosyl)ation reactions in the regulation of nuclear functions", Biochem. J, 1999, 342, pp. 249-268.

Primary Examiner — Douglas M Willis

(57) ABSTRACT

A preparation method for a compound represented by formula I or a pharmaceutically acceptable salt thereof,

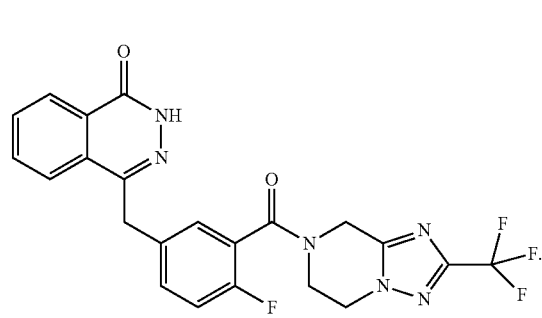

The method includes a step of reacting a compound represented by formula II

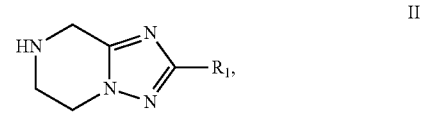

with an inorganic or organic acid selected from the group consisting of hydrochloric acid, phosphoric acid and maleic acid to provide a compound represented by formula II'

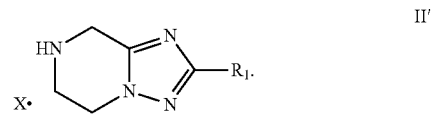

In the above formulas II and II', $R_1$ may be trifluoromethyl; and X may be hydrochloric acid, phosphoric acid, or maleic acid. The method also includes a step of reacting the compound represented by formula II' with a compound represented by formula IV:

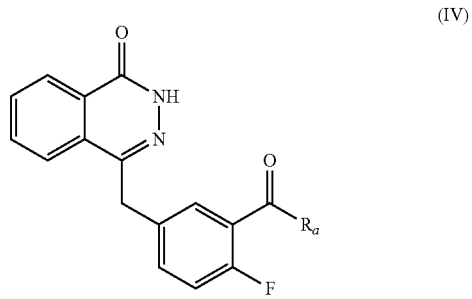

to provide the compound represented by formula I, wherein $R_a$ is selected from hydroxyl, halogen or alkoxy.

3 Claims, No Drawings

(56) References Cited

U.S. PATENT DOCUMENTS

2013/0131068 A1 5/2013 Tang et al.
2016/0151367 A1 6/2016 Tang et al.

FOREIGN PATENT DOCUMENTS

| WO | 2004032836 A2 | 4/2004 |
| WO | 2009025784 A1 | 2/2009 |
| WO | WO-2017192961 A1 | 11/2017 |

PROCESS FOR PREPARING 4-(4-FLUORO-3-(2-(TRIFLUOROMETHYL)-5,6,7,8-TETRAHYDRO-[1,2,4]TRIAZOLO[1,5-A]PYRAZINE-7-CARBONYL)BENZYL)PHTHALAZIN-1(2H)-ONE

CROSS-REFERENCE TO RELATED APPLICATIONS

The present application is a 371 National Phase of International Application No. PCT/CN2019/070797, filed on Jan. 8, 2019, which claims the benefits of Chinese Patent Application No. CN201810019736.1 filed on Jan. 9, 2018 and Chinese Patent Application No. CN201811547590.4 filed on Dec. 18, 2018, the contents of which are incorporated herein by reference in their entireties.

FIELD

The present disclosure pertains to pharmaceutical field, specifically relates to a preparation method for a PARP inhibitor and an intermediate thereof.

BACKGROUND

In recent years, the cancer mortality in our country was clearly on the rise. People's life and quality of life were threatened seriously with cancer. For the proliferation of malignant tumors, chemotherapy with traditional chemotherapy drugs or radiotherapy has high toxicity and low specificity. Thus, it is a challenging and significant project to develop anticancer drugs with high efficacy and low toxicity in the life sciences nowadays. Scientific research shows that tumor cells have specific DNA repair mechanisms, which can respond quickly and repair damages to the chromosome relevant to proliferation regulation, thereby saving them from cytotoxic effects of some therapeutic drugs and keeping them alive. The cytotoxic effect of DNA damage agents can be improved by way of tumor cell-specificity through regulating the repair mechanism for DNA damage. PARPs (Poly(ADP-ribose) polymerases), characterized by polyadenosine diphosphate-ribosylation activity, constitute a superfamily of 18 nucleus enzymes and cytoplasmic enzymes. Such poly polyadenosine diphosphate-ribosylation effect can adjust the activity of the targeted proteins and the interaction between proteins, and regulate many fundamental biological processes, including DNA repair and cell death. In addition, it is also relevant to genomic stability (see D'Amours et al. *Biochem. J*, 1999, 342, 249). Since DNA damage repair mechanism is the main mechanism that tumor cells develop tolerance to chemotherapeutic drugs and ionizing radiation treatment, PARP is considered to be an effective target to explore new methods of cancer therapy.

At present, a series of PARP inhibitors have been disclosed. Among them, CN102686591A discloses an effective PARP inhibitor represented by formula I and a preparation method thereof. The compound has significant advantages in drug efficacy.

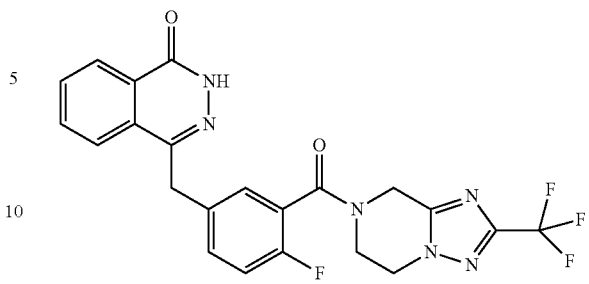

I

In the preparation process of the compound represented by formula I, a compound represented by formula II was employed as a key intermediate, and the yield and purity of the intermediate directly affected the yield and purification difficulty of the final product.

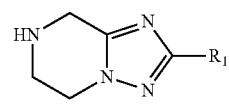

II

The existing preparation methods for this intermediate have some drawbacks. WO2004032836 discloses a preparation method for the compound represented by formula II. In some methods, column chromatography is employed for post-treatment with low efficiency, and additionally the obtained compound of formula II still contains some impurities which are difficult to be removed and would be introduced into the reaction of the final product to affect the purity of the final product. In some methods, purification was performed through protecting the imino group with BOC followed by deprotection, but this method has numerous reaction steps and a low yield. In addition, the above methods have a low reaction yield, time-consuming post-treatment and high cost when used in industrial production, and additionally the palladium catalyst used in the hydrogenation reaction cannot be completely removed, which further affects the purity of the product. Therefore, there is an urgent need for an industrial method for preparing the compound represented by formula II with a high yield, good product purity and simple post-treatment.

SUMMARY

In order to overcome the drawback existing in prior art, the purpose of the present disclosure is to provide a novel preparation method for a PARP inhibitor and an intermediate thereof.

The present disclosure provides a preparation method for a compound represented by formula II',

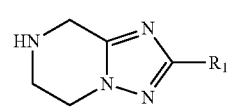

II

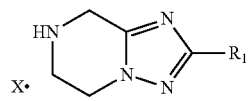

II' wherein:

$R_1$ is selected from hydrogen, alkyl, halogen, hydroxyl, cyano, alkoxy, cycloalkyl, heterocyclyl, aryl, heteroaryl, benzyl, —C(O)OR$_2$, —OC(O)R$_2$, —O(CH$_2$)$_n$C(O)OR$_2$, —(CH$_2$)$_n$NR$_3$R$_4$, —C(O)R$_2$, —NHC(O)R$_2$, —NR$_3$R$_4$, —OC(O)NR$_3$R$_4$ or —C(O)NR$_3$R$_4$, wherein each of the alkyl, alkoxy, cycloalkyl, heterocyclyl, aryl, heteroaryl and benzyl is independently optionally substituted by one or more substituents selected from alkyl, halogen, hydroxyl, alkoxy, cycloalkyl, heterocyclyl, aryl, heteroaryl, oxo, —C(O)OR$_2$, —OC(O)R$_2$, —O(CH$_2$)$_n$C(O)OR$_2$, —C(O)R$_2$, —NHC(O)R$_2$, —N$_3$R$_4$, —OC(O)NR$_3$R$_4$ or —C(O)NR$_3$R$_4$;

$R_2$ is selected from hydrogen, alkyl, cycloalkyl, heterocyclyl, aryl or heteroaryl, wherein each of the alkyl, cycloalkyl, heterocyclyl, aryl and heteroaryl is independently optionally substituted by one or more substituents selected from alkyl, halogen, hydroxyl, alkoxy, cycloalkyl, heterocyclyl, aryl, heteroaryl, carboxyl or carboxylate ester group;

each of $R_3$ and $R_4$ is independently selected from hydrogen, alkyl, cycloalkyl, heterocyclyl, aryl or heteroaryl, wherein each of the alkyl, cycloalkyl, heterocyclyl, aryl and heteroaryl is independently optionally substituted by one or more substituents selected from alkyl, halogen, hydroxyl, alkoxy, cycloalkyl, heterocyclyl, aryl, heteroaryl, carboxyl or carboxylate ester group;

or, $R_3$ and $R_4$ together with the nitrogen atom to which they are attached form heterocyclyl, wherein the heterocyclyl contains one or more heteroatoms selected from N, O, or S(O)$_m$, and the heterocyclyl is optionally substituted by one or more substituents selected from alkyl, halogen, hydroxyl, alkoxy, cycloalkyl, heterocyclyl, aryl, heteroaryl, carboxyl or carboxylate ester group;

m is selected from 0, 1 or 2;

n is selected from 0, 1 or 2;

X is an acid, which can be an inorganic acid or an organic acid; the inorganic acid can be hydrochloric acid, sulfuric acid, phosphoric acid, hydrobromic acid, trifluoroacetic acid and the like, and the organic acid can be formic acid, acetic acid, sulfonic acid, optionally substituted alkylsulfonic acid, succinic acid, maleic acid, tartaric acid, citric acid, lactic acid, oxalic acid, gluconic acid, fumaric acid, malonic acid, malic acid and the like, preferably hydrochloric acid, phosphoric acid and maleic acid, more preferably hydrochloric acid.

The method comprises a step of reacting a compound represented by formula II with a corresponding acid.

In some embodiments, $R_1$ is —CF$_3$.

The solvent used in the step of reacting a compound represented by formula II with a corresponding acid can be a conventional solvent, for example, one or more solvents selected from dimethylformamide, 1-methyl-2-pyrrolidone, dimethyl sulfoxide, tetrahydrofuran, ethyl acetate, dioxane, toluene, dimethyl sulfoxide, diethyl ether, isopropyl ether, methyl tert-butyl ether, dichloromethane, chloroform, acetone, acetonitrile, methanol, ethanol, isopropanol and water, preferably one or more solvents selected from tetrahydrofuran, ethyl acetate, dioxane, toluene, dimethyl sulfoxide, diethyl ether, isopropyl ether, dichloromethane, chloroform, acetone, acetonitrile, methanol, ethanol and isopropanol.

The molar ratio of the compound represented by formula II to the corresponding acid can be 1:1 to 1:10.

In some embodiments, the compound represented by formula II' can be subjected to isolation. The isolation method can be a conventional method, such as filtration, solvent removal and the like. Before or after the isolation of the compound represented by formula II', a purification, such as recrystallization, slurrying, column chromatography and the like, can be optionally carried out.

In some embodiments, the method comprises a step of carrying out a hydrogenation reduction reaction of a compound represented by formula III to obtain the compound represented by formula II;

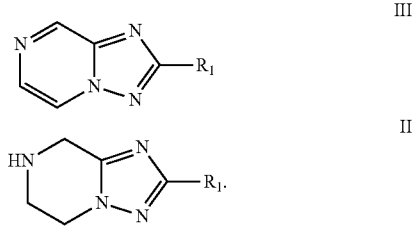

The solvent used in the step of carrying out a hydrogenation reduction reaction of a compound represented by formula III to obtain the compound represented by formula II can be a conventional solvent, such as one or more solvents selected from dimethylformamide, 1-methyl-2-pyrrolidone, dimethyl sulfoxide, tetrahydrofuran, ethyl acetate, dioxane, toluene, dimethyl sulfoxide, diethyl ether, isopropyl ether, methyl tert-butyl ether, dichloromethane, chloroform, acetone, acetonitrile, methanol, ethanol, isopropanol and water, preferably one or more solvents selected from methanol, ethanol and isopropanol.

The hydrogenation reduction reaction is preferably carried out in the presence of a catalyst; the catalyst can be a palladium-containing catalyst, such as palladium on carbon.

The present disclosure also provides a preparation method for a compound represented by formula I or a pharmaceutically acceptable salt thereof, wherein the method comprises a step of the preparation method for the compound represented by formula II' as described herein;

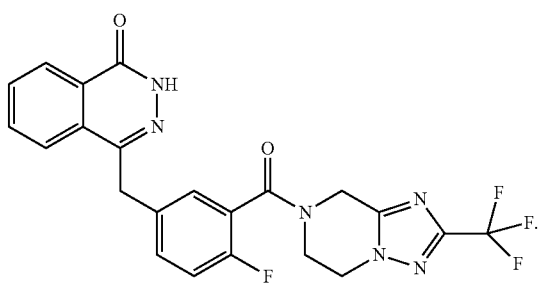

In some embodiments, the method comprises a step of reacting a compound represented by formula II' with a compound represented by formula IV,

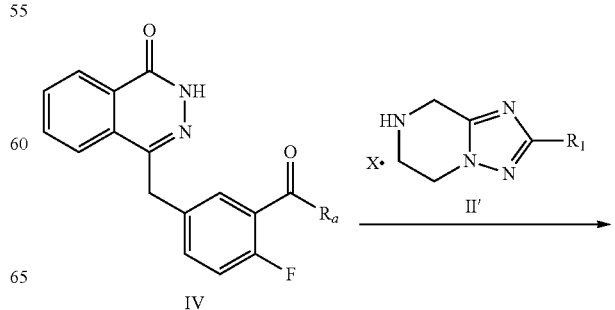

-continued

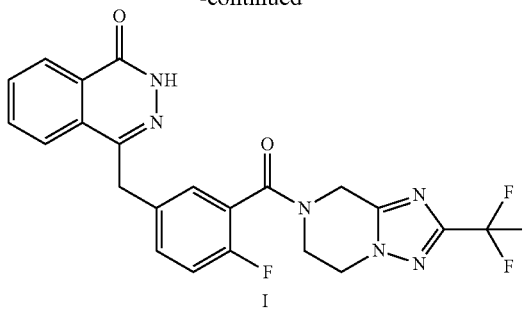

wherein $R_a$ is selected from hydroxyl, halogen or alkoxy.

The present disclosure also provides a purification method for a compound represented by formula II, wherein the method comprises carrying out a reaction of a compound represented by formula II and a corresponding acid to obtain a compound represented by formula II', isolating the compound represented by formula II', and converting the compound represented by formula II' to the compound represented by formula II.

In some embodiments, $R_1$ is —$CF_3$.

The solvent used in the reaction can be a conventional solvent, for example, one or more solvents selected from dimethylformamide, 1-methyl-2-pyrrolidone, dimethyl sulfoxide, tetrahydrofuran, ethyl acetate, dioxane, toluene, dimethyl sulfoxide, diethyl ether, isopropyl ether, methyl tert-butyl ether, dichloromethane, chloroform, acetone, acetonitrile, methanol, ethanol, isopropanol and water, preferably one or more solvents selected from tetrahydrofuran, ethyl acetate, dioxane, toluene, dimethyl sulfoxide, diethyl ether, isopropyl ether, dichloromethane, chloroform, acetone, acetonitrile, methanol, ethanol and isopropanol.

The molar ratio of the compound represented by formula II to the corresponding acid can be 1:1 to 1:10.

The isolation method can be a conventional method, such as filtration, solvent removal and the like. Before or after isolating the compound represented by formula II', a purification, such as recrystallization, slurrying, column chromatography and the like, can be optionally carried out.

The conversion method can be a conventional method, for example, reacting the compound represented by formula II' with a base, and the base can be an inorganic base or an organic base, such as sodium hydroxide, potassium hydroxide, ammonium hydroxide and the like.

In some embodiments, the compound represented by formula II is obtained from the hydrogenation reduction reaction of the compound represented by formula III.

The present disclosure also provides a preparation method for a compound represented by formula I or a pharmaceutically acceptable salt thereof, wherein the method comprises a step of the purification method for the compound represented by formula II as described herein.

In some embodiments, the method comprises a step of reacting the compound represented by formula II with the compound represented by formula IV, wherein $R_a$ is selected from hydroxyl, halogen or alkoxy.

In the preparation method for the intermediate of PARP inhibitor of the present disclosure, it is unexpected that, by employing a salt-forming purification method, the reaction yield and purity are improved greatly, the product processing time in the production process is shortened and the production efficiency is greatly increased. The intermediate after forming a salt is in solid form and has a suitable solubility so that it can be purified by a conventional method such as recrystallization and slurrying to improve the purity thereof and effectively prevent the introduction of impurities originated from the reactions to the final product, and therefore the method has advantages in the reaction and purification of the final product.

Unless stated to the contrary, the terms used in the specification and the claims have the meanings described below.

The term "alkyl" refers to a saturated aliphatic hydrocarbon group, which is a straight or branched chain group comprising 1 to 20 carbon atoms, preferably an alkyl comprising 1 to 12 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof. The alkyl is more preferably a lower alkyl comprising 1 to 6 carbon atoms, non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl can be substituted or unsubstituted, and when the alkyl is substituted, the substituent can be substituted at any available connection site, and the substituent is preferably one or more groups independently selected from alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio, oxo, carboxyl and carboxylate ester group.

The term "cycloalkyl" refers to a saturated or partially unsaturated monocyclic or polycyclic hydrocarbon substituent group comprising 3 to 20 carbon atoms, preferably 3 to 12 carbon atoms, more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like. Polycyclic cycloalkyl includes a cycloalkyl comprising a spiro ring, a fused ring or a bridged ring.

The term "heterocyclyl" refers to a saturated or partially unsaturated monocyclic or polycyclic hydrocarbon substituent group containing 3 to 20 ring atoms, wherein one or more ring atoms are heteroatoms selected from N, O and $S(O)_m$ (wherein m is an integer of 0 to 2), but excluding —O—O—, —O—S— or —S—S— in the ring, and the remaining ring atoms are carbon atoms. Preferably, the heterocyclyl contains 3 to 12 ring atoms wherein 1 to 4 atoms are heteroatoms; more preferably, the heterocyclyl contains 3 to 6 ring atoms. Non-limiting examples of monocyclic heterocyclyl include pyrrolidinyl, imidazolidinyl, tetrahydrofuranyl, tetrahydrothienyl, dihydroimidazolyl, dihydrofuryl, dihydropyrazolyl, dihydropyrrolyl, piperidinyl, piperazinyl, morpholinyl, thiomorpholinyl, homopiperazinyl and the like, and preferably piperidinyl or pyrrolidinyl. Polycyclic heterocyclyl includes heterocyclyl comprising a spiro ring, a fused ring or a bridged ring.

The term "aryl" refers to a 6 to 14 membered all-carbon monocyclic ring or fused polycyclic ring (that is, ring shares an adjacent pair of carbon atoms) having a conjugated π-electron system, preferably 6 to 10 membered aryl, for example, phenyl and naphthyl. The aryl ring can be fused to a heteroaryl ring, a heterocyclyl ring or a cycloalkyl ring, wherein the ring connected to the parent structure is an aryl ring, and non-limiting examples of aryl include:

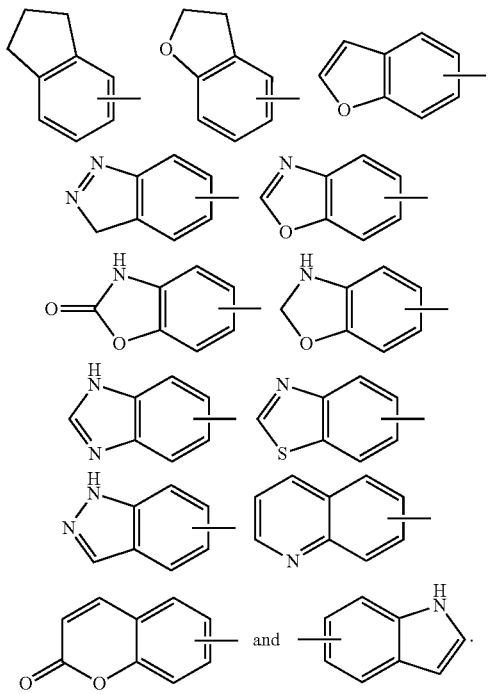

The aryl can be substituted or unsubstituted, and when substituted, the substituent is preferably one or more groups independently selected from alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio, carboxyl and carboxylate ester group, preferably phenyl.

The term "heteroaryl" refers to a 5 to 14 membered heteroaromatic system comprising 1 to 4 heteroatoms selected from O, S and N. The heteroaryl is preferably 5 to 12 membered heteroaryl, for example, imidazolyl, furyl, thienyl, thiazolyl, pyrazolyl, oxazolyl, pyrrolyl, tetrazolyl, pyridyl, pyrimidinyl, thiadiazolyl, pyrazinyl and the like, preferably imidazolyl, pyrazolyl, pyrimidinyl or thiazolyl; more preferably pyrazolyl or thiazolyl. The heteroaryl ring can be fused to an aryl ring, a heterocyclyl ring or a cycloalkyl ring, wherein the ring connected to the parent structure is a heteroaryl ring and non-limiting examples of heteroaryl include:

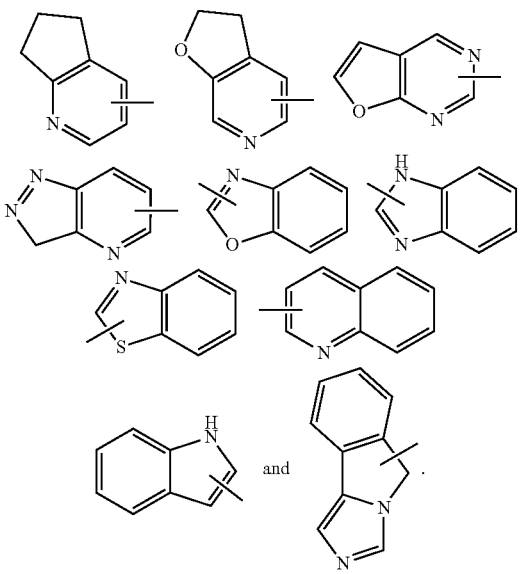

The heteroaryl can be optionally substituted or unsubstituted, and when substituted, the substituent is preferably one or more groups independently selected from alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio, carboxyl and carboxylate ester group.

The term "alkoxy" refers to —O-(alkyl) or —O-(unsubstituted cycloalkyl), wherein the alkyl is as defined above. Non-limiting examples of alkoxy include: methoxy, ethoxy, propoxy, butoxy, cyclopropyloxy, cyclobutyloxy, cyclopentyloxy, cyclohexyloxy. The alkoxy can be optionally substituted or unsubstituted, and when substituted, the substituent is preferably one or more groups independently selected from alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio, carboxyl and carboxylate ester group.

The term "halogen" refers to fluorine, chlorine, bromine or iodine.

The term "hydroxyl" refers to —OH group.

The term "amino" refers to —NH$_2$.

The term "cyano" refers to —CN.

The term "nitro" refers to —NO$_2$.

The term "benzyl" refers to —CH$_2$-phenyl.

The term "oxo" refers to =O.

The term "carboxyl" refers to —C(O)OH.

The term "carboxylate ester" refers to —C(O)O(alkyl) or —C(O)O(cycloalkyl).

"Optional" or "optionally" means that the event or circumstance described subsequently can, but does not have to occur, and such a description includes the situation in which the event or circumstance occurs or does not occur. For example, "heterocyclyl optionally substituted by alkyl" means that alkyl can, but does not have to exist, and such a description includes the situation that the heterocyclyl is substituted by alkyl and the situation that the heterocyclyl is not substituted by alkyl.

In the chemical structure of the compound of the present disclosure, the bond "╱" does not specify a configuration, that is, if configurational isomerism exists in the chemical structure, the bond "╱" can be "╲╲╲" or "▲", or it can contain both "╲╲╲" and "▲" configuration.

DETAILED DESCRIPTION

The following will explain the present disclosure in detail with specific embodiments, so that those skilled in the art can more fully understand the present disclosure. The specific embodiments are only intended for illustrating the technical solutions of the present disclosure, but the present disclosure is not limited thereto.

According to a First Embodiment

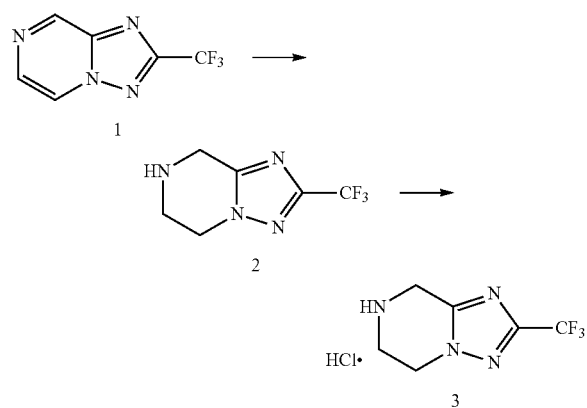

To a reactor were added 5.0 kg of Compound 1, 250 g of 10% palladium on carbon and 80 L of methanol, and the hydrogenation reaction was carried out under 0.41 MPa at 25° C. for 24 hours. The palladium on carbon was removed by filtration and the filter cake was washed with methanol. The filtrate was collected and evaporated to dryness under reduced pressure, followed by addition of 20 L of ethyl acetate to the obtained concentrate. After the solid was dissolved by stirring, the mixture was cooled to 0° C. in an ice-water bath, adjusted to pH of 2-3 with 4 M hydrogen chloride in ethyl acetate, stirred and filtered. The filter cake was slurried with 20 L of ethyl acetate at room temperature for 3 to 4 hours. The mixture was filtered and the filter cake was dried under vacuum at 45° C. for 6-8 hours to obtain 5.5 kg of Compound 3 as a solid with a yield of 91.7% and a HPLC purity of 99.69%.

According to a Second Embodiment

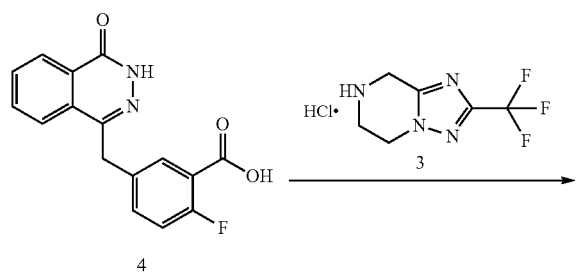

-continued

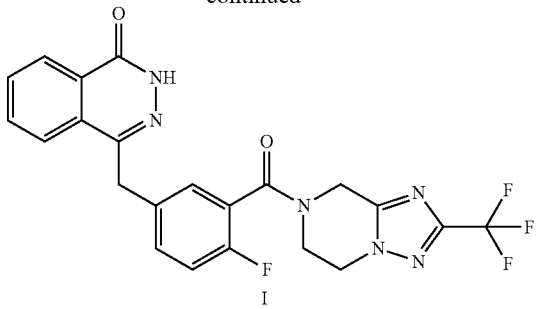

According to the method of Embodiment 19 in CN102686591A, 2 g of the obtained Compound 3 and 2.79 g of Compound 4 were reacted to obtain 3.6 g of the compound represented by formula I with a yield of 87.8%.

According to a Third Embodiment

At room temperature, 2.0 g of Compound 2 (prepared according to the method disclosed in WO2009025784) was dissolved in 30 mL of isopropanol, followed by dropwise addition of concentrated sulfuric acid to adjust the pH to 3 while stirring. The resulting mixture was stirred at room temperature, and no solid was precipitated out. The mixture was then poured into 150 mL of n-hexane, and further stirred at room temperature. No solid was precipitated out, and Compound 2 sulfate salt in solid form could not be obtained.

According to a Fourth Embodiment

At room temperature, 1.11 g of Compound 2 was dissolved in 10 mL of isopropanol, followed by dropwise addition of 15% phosphoric acid/isopropanol solution to adjust the pH to 3 while stirring. The resulting mixture was stirred at room temperature and filtered. The filter cake was washed with isopropanol and dried under vacuum to obtain 1.46 g of Compound 2 phosphate salt in solid form with a yield 87.1% and a HPLC purity of 99.72%.

According to a Fifth Embodiment

At room temperature, 1.28 g of Compound 2 was dissolved in 10 mL of isopropanol, followed by dropwise addition of 20% acetic acid/isopropanol solution to adjust the pH to 3 while stirring. The resulting mixture was stirred at room temperature, and no solid was precipitated out. The mixture was poured into 100 mL of n-hexane, and further stirred at room temperature. No solid was precipitated out, and Compound 2 acetate salt in solid form could not be obtained.

According to a Sixth Embodiment

At room temperature, 1.05 g of Compound 2 was dissolved in 10 mL of isopropanol, followed by dropwise addition of 15% citric acid/isopropanol solution to adjust the pH to 3 while stirring. The resulting mixture was stirred at room temperature and no solid was precipitated out. The mixture was poured into 100 mL of n-hexane, and further stirred at room temperature. No solid was precipitated out, and Compound 2 citrate salt in solid form could not be obtained.

According to a Seventh Embodiment

At room temperature, 1.12 g of Compound 2 was dissolved in 10 mL of isopropanol, followed by addition of 0.74 g of maleic acid while stirring. The resulting mixture was stirred at room temperature and filtered. The filter cake was washed with isopropanol and dried under vacuum to obtain 1.51 g of Compound 2 maleate salt in solid form with a yield 84.6%.

Since the present disclosure has been described according to its particular embodiments, certain modifications and equivalent variations will be apparent to those skilled in the art and are included within the scope of the present disclosure.

The invention claimed is:

1. A process for preparing a compound represented by formula I:

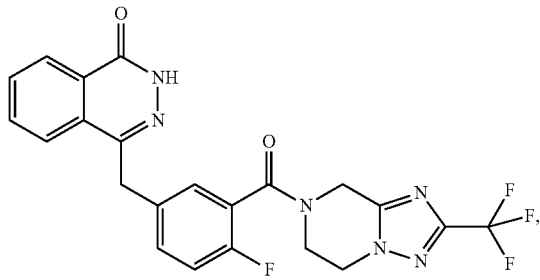

I wherein the process comprises the following steps:
(1) reacting a compound represented by formula II:

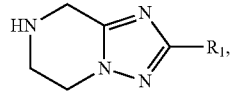

II wherein:
$R_1$ is trifluoromethyl;
with an inorganic acid or organic acid selected from the group consisting of hydrochloric acid, maleic acid, and phosphoric acid, to provide a compound represented by formula II':

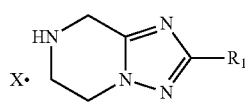

II' wherein:
$R_1$ is trifluoromethyl; and
X is hydrochloric acid, maleic acid, or phosphoric acid, (2) reacting the compound represented by formula II' above with a compound represented by formula IV:

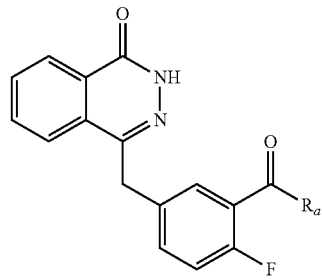

IV wherein
$R_a$ is halogen, hydroxy, or alkoxy;
to provide the compound represented by formula I:

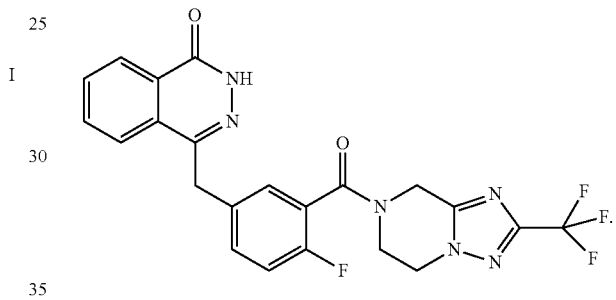

I

2. The process according to claim 1, wherein X is hydrochloric acid.

3. A process for preparing a compound represented by formula I:

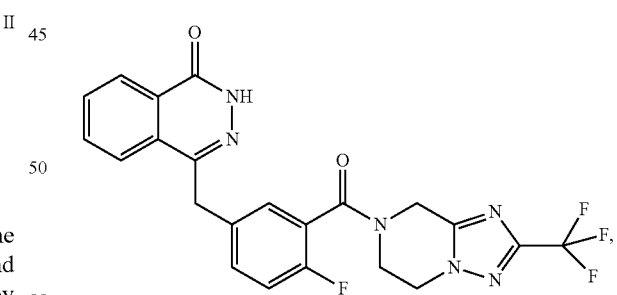

I wherein the process comprises the following steps:

(1) reacting a compound represented by formula II:

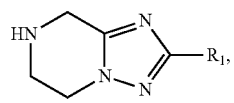

II wherein

R$_1$ is trifluoromethyl;

with an inorganic acid or organic acid selected from the group consisting of hydrochloric acid, maleic acid, and phosphoric acid, to provide a compound represented by formula II':

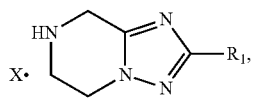

II' wherein

R$_1$ is trifluoromethyl; and

X is hydrochloric acid, maleic acid, or phosphoric acid;

(2) reacting the compound represented by formula II' above with an inorganic base or an organic base selected from the group consisting of ammonium hydroxide, sodium hydroxide, and potassium hydroxide, to provide the compound represented by formula II above; and (3) reacting the compound represented by formula II above with a compound represented by formula IV:

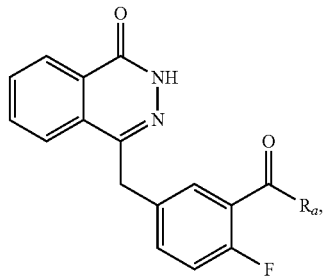

IV wherein
R$_a$ is halogen hydroxy, or alkoxy;
to provide the compound represented by formula I:

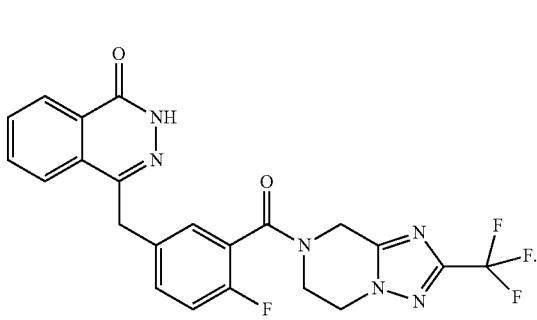

I

* * * * *